United States Patent
Jung et al.

(10) Patent No.: US 9,969,830 B2
(45) Date of Patent: May 15, 2018

(54) OXAZOLINE MODIFIED COPOLYMER, COMPOSITION INCLUDING OXAZOLINE MODIFIED COPOLYMER, AND ARTICLE MANUFACTURED FROM THE COMPOSITION

(71) Applicants: SAMSUNG ELECTRONICS CO., LTD., Suwon-si, Gyeonggi-do (KR); TECHNISCHE UNIVERSITAET DRESDEN, Dresden (DE)

(72) Inventors: Won Cheol Jung, Seoul (KR); In Ki Kim, Hwaseong-si (KR); Moo Ho Lee, Suwon-si (KR); Rainer Jordan, Dresden (DE); Erik Wegener, Dresden (DE)

(73) Assignees: SAMSUNG ELECTRONICS CO., LTD., Gyeonggi-Do (KR); TECHNISCHE UNIVERSITAET DRESDEN, Dresden (DE)

( * ) Notice: Subject to any disclaimer, the term of this patent is extended or adjusted under 35 U.S.C. 154(b) by 50 days.

(21) Appl. No.: 15/270,675

(22) Filed: Sep. 20, 2016

(65) Prior Publication Data
US 2017/0342184 A1    Nov. 30, 2017

(51) Int. Cl.
*C08F 226/02* (2006.01)
*A01N 37/20* (2006.01)
(Continued)

(52) U.S. Cl.
CPC ............ *C08F 226/02* (2013.01); *A01N 37/20* (2013.01); *C08F 212/08* (2013.01); *C08F 220/10* (2013.01); *C08L 23/12* (2013.01)

(58) Field of Classification Search
CPC .......... C08F 12/08; C08F 20/10; C08F 20/12; C08F 20/14; C08G 73/0233
See application file for complete search history.

(56) References Cited

U.S. PATENT DOCUMENTS 6,444,776 B1 * 9/2002 Holland ................. C08G 77/26
                                                  264/331.11
2008/0185332 A1 * 8/2008 Niu ..................... B01D 67/0083
                                                  210/500.38
(Continued)

FOREIGN PATENT DOCUMENTS

CN    101787167 A    7/2010
EP    1739143 A1     1/2007
(Continued)

OTHER PUBLICATIONS

"Synthesis and Surfactant Property of Copolymers having a Poly(2-oxazoline) Graft Chain" authored by Shoda et al. and published in the Journal of Polymer Science, Part A: Polymer Chemistry (1992) 30, 1489-1494.*
(Continued)

*Primary Examiner* — Marc S Zimmer
(74) *Attorney, Agent, or Firm* — Cantor Colburn LLP

(57) ABSTRACT

A copolymer includes a first structural unit selected from Chemical Formula 1, Chemical Formula 2, and a combination thereof and a second structural unit selected from Chemical Formula 3, Chemical Formula 4, and a combination thereof; and a composition including the copolymer and an article manufactured from the composition are provided.

Chemical Formula 1

(Continued)

-continued

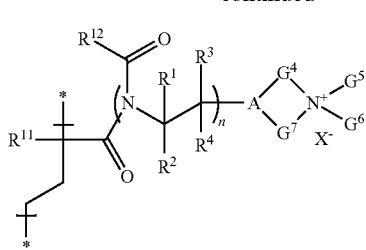

Chemical Formula 2

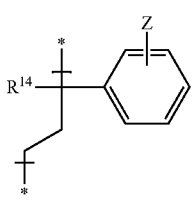

Chemical Formula 3

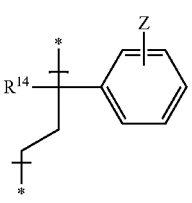

Chemical Formula 4

Definitions of Chemical Formulae 1 to 4 are the same as described in the detailed description.

20 Claims, 2 Drawing Sheets

(51) Int. Cl.
  C08L 23/12 (2006.01)
  C08F 220/10 (2006.01)
  C08F 212/08 (2006.01)

(56) References Cited

U.S. PATENT DOCUMENTS

| 2011/0123475 | A1 | 5/2011 | Dias et al. |
| 2015/0166796 | A1 | 6/2015 | Sun et al. |
| 2015/0274891 | A1 | 10/2015 | Konradi et al. |
| 2015/0328588 | A1 | 11/2015 | Schmidt-Leithoff et al. |

FOREIGN PATENT DOCUMENTS

| JP | 2011140562 | 7/2011 |
| KR | 1020150096485 A | 8/2015 |
| WO | 2012175923 A1 | 12/2012 |
| WO | 2014155156 A1 | 10/2014 |

OTHER PUBLICATIONS

Influence of Satellite Groups on Telechelic Antimicrobial Functions of Polyoxazolines authored by Tiller et al. and published in Macromolecular Bioscience (2005) 5, 149-156.*

Franck Hui, et al., "Antimicrobial N-Halamine Polymers and Coatings: A Review of Their Synthesis, Characterization, and Applications", Biomacromolecules 2013, 14, 585-601.

Matthias Holderle, et al., "Morphology and Crafting of Oxazoline-Functional Polymer Particles with Various Carboxylic Acids", Polymer Chemistry, vol. 36, 1821-1827 (1998).

Tommi Vainio, et al., "Functionalization of Polypropylene with Oxazoline and Reactive Blending of PP with PBT in a Corotating Twin-Screw Extruder", John Wiley & Sons, Inc. 1997, 883-894.

Vanessa G. Correia, et al., "Oxazoline-Based Antimicrobial Oligomers: Synthesis by CROP Using Supercritical Co2a", Macromol. Biosci. 2011, 11, 1128-1137.

* cited by examiner

# OXAZOLINE MODIFIED COPOLYMER, COMPOSITION INCLUDING OXAZOLINE MODIFIED COPOLYMER, AND ARTICLE MANUFACTURED FROM THE COMPOSITION

BACKGROUND

1. Field

Embodiments relate to an oxazoline-based copolymer, a composition including the same, and an article manufactured from the composition.

2. Description of the Related Art

Recently, antimicrobial functionality and antifouling functionality are increasingly demanded in interior or exterior materials of electronic products such as a laundry machine, a refrigerator, an air conditioner, a mobile phone, a medical device, a 3D printing product, and other home appliances.

For example, an antimicrobial technique includes adding a metal compound including Zn or the like having an antimicrobial property to an electronic product to provide an antimicrobial functionality. However, the antimicrobial additive may sometimes leach into the human body and has insufficient durability.

In addition, the antimicrobial functionality may also be provided by adding to or coating an electronic product with a polymer including N-halamine. However, the technique has drawbacks including performing a regeneration process and repeatedly adding halogen material.

A fluorine coating is also used for antifouling. However, the technique is expensive, involves a complicated synthesis process, and the resulting coating has insufficient durability. Such a coating may not be suitable for economically providing durability to the interior or exterior material of a home appliance.

Thus, it is desirable to develop materials capable of being extruded and injected so that the antimicrobial/antifouling component is not leached therefrom, and that an antimicrobial/antifouling functionality is imparted thereto.

SUMMARY

Provided is a material capable of being processed by extrusion and injection molding, that is durable, is not consumed when providing antimicrobial activity, and compatible with a polymer resin, that can be imparted with an antimicrobial/antifouling functionality, and that doesn't lose its antimicrobial/antifouling functionality through a leaching process; and an article produced therefrom.

In an embodiment, a copolymer includes a first structural unit selected from Chemical Formula 1, Chemical Formula 2, and a combination thereof and a second structural unit selected from Chemical Formula 3, Chemical Formula 4, and a combination thereof.

Chemical Formula 1

Chemical Formula 2

In Chemical Formulae 1 and 2, $R^{11}$ is a hydrogen atom or a methyl group, A is a nitrogen, $R^{12}$ is a substituted or unsubstituted C1 to C10 alkyl group, a substituted or unsubstituted C3 to C20 cycloalkyl group, a substituted or unsubstituted C6 to C20 aryl group, or a substituted or unsubstituted C3 to C20 heterocyclic group, $R^1$ to $R^4$ are the same or different, and are independently hydrogen, a halogen, a hydroxy group, or a substituted or unsubstituted C1 to C5 alkyl group, n is an average value and a real number of 1 to 200, $G^1$, $G^2$, $G^3$, $G^5$, and $G^6$ are the same or different, and are independently a substituted or unsubstituted C1 to C30 alkyl group, a substituted or unsubstituted C3 to C20 cycloalkyl group, a substituted or unsubstituted C6 to C20 aryl group, or a substituted or unsubstituted C3 to C20 heterocyclic group, $G^4$ and $G^7$ are the same or different, and are independently a substituted or unsubstituted C1 to C10 alkylene group, and $X^-$ is a halide ion, a hydroxide ion, a fluorinated boron ion, a nitrate ion, a phosphate salt ion, a trifluoroacetate ion, or a sulfate ion.

Chemical Formula 3

In Chemical Formula 3, $R^{13}$ is a hydrogen atom or a methyl group, and Y is a substituted or unsubstituted C1 to C30 alkyl group, a substituted or unsubstituted C3 to C30 cycloalkyl group, a substituted or unsubstituted C6 to C30 aryl group, or a substituted or unsubstituted C3 to C30 heterocyclic group.

Chemical Formula 4

In Chemical Formula 4, $R^{14}$ is a hydrogen atom or a methyl group, and Z is a hydrogen atom, a substituted or unsubstituted C1 to C30 alkyl group, or a halogen atom.

In Chemical Formula 1 or 2, $R^{12}$ may be a C1 to C5 alkyl group.

At least one of $G^1$ to $G^3$ in Chemical Formula 1 or at least one of $G^5$ and $G^6$ in Chemical Formula 2 may be a C6 to C30 alkyl group.

In Chemical Formula 1, one of $G^1$ to $G^3$ may be a C6 to C30 alkyl group and the remaining two may each independently be a C1 to C3 alkyl group.

In Chemical Formula 2, one of $G^5$ and $G^6$ may be a C6 to C30 alkyl group and the remaining one may be a C1 to C3 alkyl group.

In the copolymer, the first structural unit and the second structural unit may be present in a mole ratio of about 1:99 to about 99:1.

The Y of Chemical Formula 3 or the Z of Chemical Formula 4 may be a substituted or unsubstituted C1 to C30 alkyl group.

A mass average molecular weight of the copolymer may be about 1,000 to about 1,000,000 g/mol.

In another embodiment, a composition including the copolymer is provided.

The composition may further include at least one thermoplastic polymer selected from polyolefin, polyalkyl (meth)acrylate, polyacrylonitrile, polystyrene, polyvinyl chloride, polyvinylidene chloride, a silicone resin, polysulfone, polycarbonate, a rubber modified vinyl-based copolymer, polyamide, polyester, polyurethane, and a copolymer thereof.

The thermoplastic polymer may be present in an amount of about 1 wt % to about 99.9 wt % based on the total weight of the composition.

In the composition, the first structural unit of the copolymer may be present in an amount of about 0.1 wt % to about 50 wt %, for example about 0.5 wt % to about 10 wt %, based on the total weight of the composition.

According to another embodiment, an article included the composition is provided.

The article may be produced by extruding, co-extruding, injection molding, or double injection molding the composition.

The article may have a greater than or equal to about 85% antimicrobial rate for *Escherichia coli*, which is measured by an antimicrobial test according to ISO 22196.

The pollution level of the article may be decreased in greater than or equal to about 20% compared to the pollution level of article treated with no antifouling treatment.

A method of preparing a copolymer includes: copolymerizing a first monomer selected from Chemical Formula 11, Chemical Formula 12, and a combination thereof and a second monomer selected from Chemical Formula 13, Chemical Formula 14, and a combination thereof:

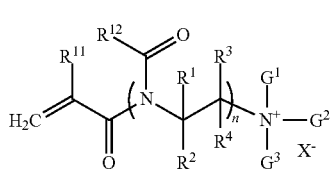

Chemical Formula 11

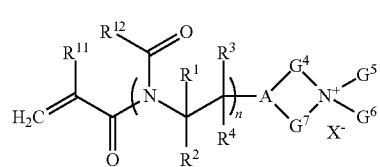

Chemical Formula 12 wherein, in Chemical Formulae 11 and 12, $R^{11}$ is a hydrogen atom or a methyl group, A is a nitrogen, $R^{12}$ is a substituted or unsubstituted C1 to C10 alkyl group, a substituted or unsubstituted C3 to C20 cycloalkyl group, a substituted or unsubstituted C6 to C20 aryl group, or a substituted or unsubstituted C3 to C20 heterocyclic group, $R^1$ to $R^4$ are the same or different, and are independently a hydrogen atom, a halogen atom, a hydroxy group, or a substituted or unsubstituted C1 to C5 alkyl group, n is an average value and a real number of 1 to 200, $G^1$, $G^2$, $G^3$, $G^5$, and $G^6$ are the same or different, and are independently a substituted or unsubstituted C1 to C30 alkyl group, a substituted or unsubstituted C3 to C20 cycloalkyl group, a substituted or unsubstituted C6 to C20 aryl group, or a substituted or unsubstituted C3 to C20 heterocyclic group, $G^4$ and $G^7$ are the same or different, and are independently a substituted or unsubstituted C1 to C10 alkylene group, and $X^-$ is a halide ion, a hydroxide ion, a fluorinated boron ion, a nitrate ion, a phosphate salt ion, a trifluoroacetate ion, or a sulfate ion,

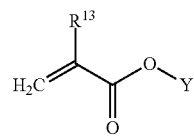

Chemical Formula 13 wherein in Chemical Formula 13, $R^{13}$ is a hydrogen atom or a methyl group, and Y is a substituted or unsubstituted C1 to C30 alkyl group, a substituted or unsubstituted C3 to C30 cycloalkyl group, a substituted or unsubstituted C6 to C30 aryl group, or a substituted or unsubstituted C3 to C30 heterocyclic group,

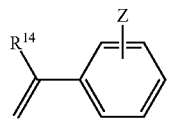

Chemical Formula 14 wherein in Chemical Formula 14, $R^{14}$ is a hydrogen atom or a methyl group and Z is a hydrogen atom, a substituted or unsubstituted linear or branched C1 to C30 alkyl group, or a halogen atom.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
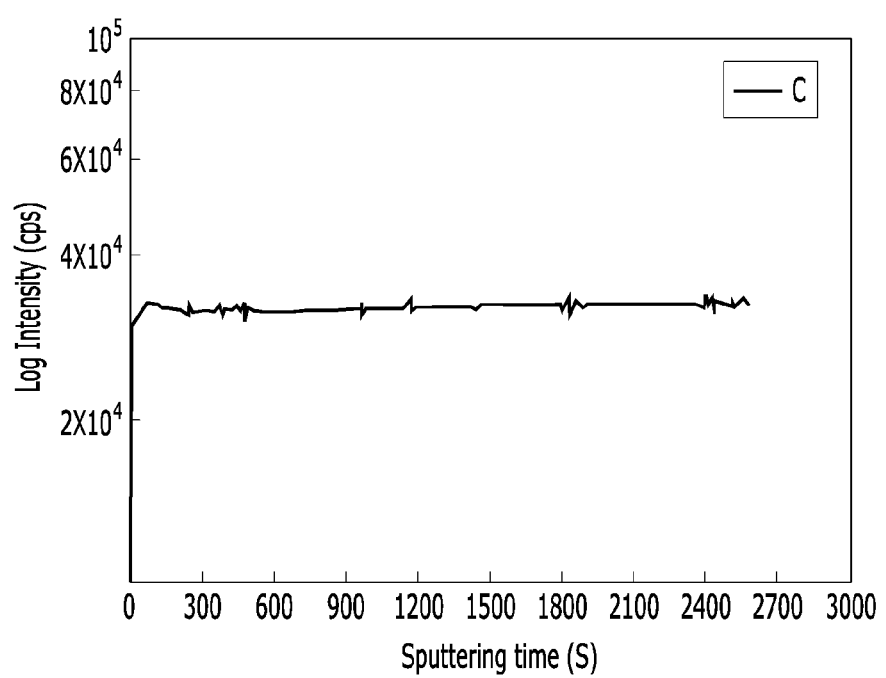
FIG. 1 is a graph of log intensity (counts per second, cps) versus sputtering time (seconds, s) and is a Time-of-Flight secondary ion mass spectrometry graph for a polypropylene injection molded specimen according to an exemplary embodiment.

Reference will now be made in detail to exemplary embodiments, examples of which are illustrated in the accompanying drawings. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. "Or" means "and/or." Expressions such as "at least one of," when preceding a list of elements, modify the entire list of elements and do not modify the individual elements of the list.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer, or section. Thus, "a first element," "component," "region," "layer," or "section" discussed below could be termed a second element, component, region, layer, or section without departing from the teachings herein.

The terminology used herein is for describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. "About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments will hereinafter be described in detail, and may be performed by those having ordinary skill in the art. However, this disclosure may be embodied in different forms and is not construed as limited to the exemplary embodiments set forth herein.

As used herein, when a definition is not otherwise provided the term "substituted" means a compound or radical substituted with at least one (e.g., 1, 2, 3, 4, 5, 6, or more) substituents independently selected from a C1 to C30 alkyl group, a C2 to C30 alkenyl or alkynyl group, a C6 to C30 aryl group, a C7 to C30 alkylaryl group, a C1 to C30 alkoxy group, a C1 to C30 heteroalkyl group, a C3 to C30 heteroalkylaryl group, a C3 to C30 cycloalkyl group, a C3 to C15 cycloalkenyl group, a C6 to C30 cycloalkynyl group, a C2 to C30 heterocycloalkyl group, a halogen (F, Cl, Br, or I), a hydroxy group (—OH), a nitro group (—$NO_2$), a cyano group (—CN), an amino group (—NRR' wherein R and R' are independently hydrogen or a C1 to C6 alkyl group), a sulfobetaine group (—RR'$N^+$($CH_2$)$_n$$SO_3^-$), a carboxyl betaine group (—RR'$N^+$($CH_2$)$_n$$COO^-$, wherein R and R' are independently a C1 to C20 alkyl group), an azido group (—$N_3$), an amidino group (—C(=NH)$NH_2$), a hydrazino group (—$NHNH_2$), a hydrazono group (=N($NH_2$)), an aldehyde group (—C(=O)H), a carbamoyl group (—C(O)$NH_2$), a thiol group (—SH), an ester group (—C(=O)OR, wherein R is a C1 to C6 alkyl group or a C6 to C12 aryl group), a carboxyl group (—COOH) or a salt thereof (—C(=O)OM, wherein M is an organic or inorganic cation), a sulfonic acid group (—$SO_3H$) or a salt thereof (—$SO_3M$, wherein M is an organic or inorganic cation), a phosphoric acid group (—$PO_3H_2$) or a salt thereof (—$PO_3MH$ or —$PO_3M_2$, wherein M is an organic or inorganic cation), or a combination including at least one of the foregoing, instead of hydrogen, provided that the substituted atom's normal valence is not exceeded.

The term "alkyl" refers to fully saturated branched or unbranched (or straight chain or linear) hydrocarbon groups. Non-limiting examples of an alkyl group include methyl, ethyl, n-propyl, isopropyl, n-butyl, isobutyl, sec-butyl, n-pentyl, isopentyl, neopentyl, iso-amyl, n-hexyl, 3-methylhexyl, 2,2-dimethylpentyl, 2,3-dimethylpentyl, and n-heptyl.

The term "cycloalkyl" refers to a monovalent group having one or more saturated rings in which all ring members are carbon (e.g., cyclopentyl and cyclohexyl).

The term "heterocycloalkyl" refers to a cycloalkyl group including at least one heteroatom selected from N, O, P, Si, and S.

The term "halogen atom" includes fluorine, bromine, chlorine, or iodine. The term "alkoxy" refers to alkyl-O—, and the alkyl group is the same as defined above. Non-limiting examples of an alkoxy group include methoxy, ethoxy, propoxy, 2-propoxy, butoxy, tert-butoxy, pentyloxy, hexyloxy, cyclopropoxy, and cyclohexyloxy.

The term "aryl" refers to an aromatic hydrocarbon system containing one or more rings. Non-limiting examples of the aryl group include phenyl, naphthyl, and tetrahydronaphthyl.

The term "heteroaryl" refers to a monocyclic or bicyclic organic compound that includes at least one heteroatom selected from N, O, P, Si, and S, and the remaining ring atoms are C. For example, the heteroaryl group may include 1 to 5 heteroatoms and may include 5 to 10 ring members, wherein S and N may be oxidized to various oxidation states.

The term "heteroaryl" also refers to a group in which a heteroaromatic ring is fused to one or more aryl, cycloalkyl, or heterocycloalkyl rings.

The term "heteroaryloxy" refers to heteroaryl-O—, and the heteroaryl group is as described above.

The terms "alkylene," "arylene," "heteroarylene," "cycloalkylene," and "heterocycloalkylene" refer to substituents, in which one hydrogen atom of an alkyl group, an aryl group, a heteroaryl group, a cycloalkyl group, or a heterocycloalkyl group is substituted with a bond.

As used herein, the term "combination thereof" may refer to a mixture, a stacked structure, a composite, a copolymer, an alloy, a blend, or a reaction product of components.

In addition, in the specification and claims, "*" may refer to a point of attachment to nitrogen, carbon, or another atom.

In an embodiment, an antimicrobial/antifouling functional copolymer includes a first structural unit selected from Chemical Formula 1, Chemical Formula 2, and a combination thereof and a second structural unit selected from Chemical Formula 3, Chemical Formula 4, and a combination thereof.

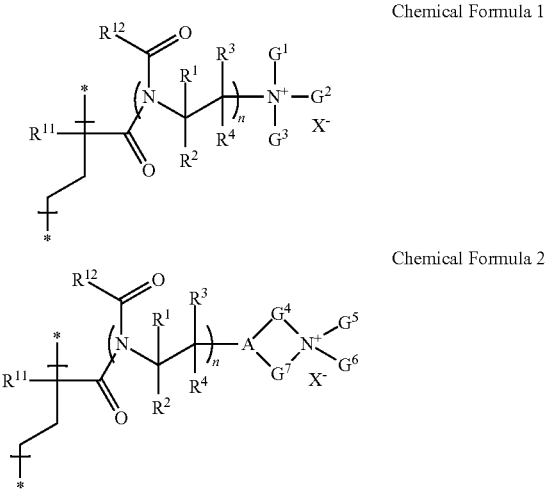

Chemical Formula 1

Chemical Formula 2

In Chemical Formulae 1 and 2, $R^{11}$ is a hydrogen atom or a methyl group, A is a nitrogen, $R^{12}$ is a substituted or unsubstituted C1 to C10 alkyl group, a substituted or unsubstituted C3 to C20 cycloalkyl group, a substituted or unsubstituted C6 to C20 aryl group, or a substituted or unsubstituted C3 to C20 heterocyclic group, $R^1$ to $R^4$ are the same or different, and are independently a hydrogen atom, a halogen atom, a hydroxy group, or a substituted or unsubstituted C1 to C5 alkyl group, n is an average value and a real number of 1 to 200, $G^1$, $G^2$, $G^3$, $G^5$, and $G^6$ are the same or different, and are independently a substituted or unsubstituted C1 to C30 alkyl group, a substituted or unsubstituted C3 to C20 cycloalkyl group, a substituted or unsubstituted C6 to C20 aryl group, or a substituted or unsubstituted C3 to C20 heterocyclic group, $G^4$ and $G^7$ are the same or different, and are independently a substituted or unsubstituted C1 to C10 alkylene group, and $X^-$ is a halide ion, a hydroxide ion, a fluorinated boron ion, a nitrate ion, a phosphate salt ion, a trifluoroacetate ion, or a sulfate ion.

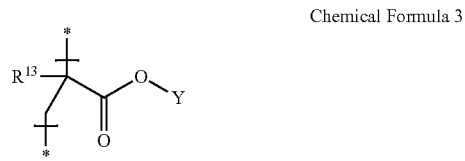

Chemical Formula 3

In Chemical Formula 3, $R^{13}$ is a hydrogen atom or a methyl group and Y is a substituted or unsubstituted C1 to C30 alkyl group, a substituted or unsubstituted C3 to C30 cycloalkyl group, a substituted or unsubstituted C6 to C30 aryl group, or a substituted or unsubstituted C3 to C30 heterocyclic group.

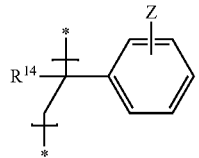

Chemical Formula 4

In Chemical Formula 4, $R^{14}$ is a hydrogen atom or a methyl group, Z is a hydrogen atom, a substituted or unsubstituted C1 to C30 alkyl group, or a halogen atom.

The first structural unit includes the structural unit represented by Chemical Formula 1, the structural unit represented by Chemical Formula 2, or the combination thereof. For example, the first structural unit may be the structural unit represented by Chemical Formula 1, the structural unit represented by Chemical Formula 2, or a combined structural unit of the structural units represented by Chemical Formula 1 and Chemical Formula 2.

Likewise, the second structural unit includes the structural unit represented by Chemical Formula 3, the structural unit represented by Chemical Formula 4, or the combination thereof. For example, the second structural unit may be the structural unit represented by Chemical Formula 3, the structural unit represented by Chemical Formula 4, or a combined structural unit of the structural units represented by Chemical Formula 3 and Chemical Formula 4.

The copolymer has antimicrobial (bio-killing) functions to suppress the propagation of bacteria, and antifouling (bio-repelling) functions to prevent the attachment of bacteria, and has good compatibility with a polymer resin and may be employed in extrusion or injecting molding processes. The copolymer may be added during extruding, co-extruding, or injecting, or double injecting the polymer, so as to act as an additive for providing antimicrobial/antifouling characteristics.

In the copolymer, the first structural unit may impart antimicrobial/antifouling functionality; and the second structural unit may act to improve compatibility with a polymer resin. In the first structural unit, the oxazoline group is hydrophilic and has antifouling functionality. The hydrophilic oxazoline groups may provide for a durable material for use in a damp environment such as a washing machine, or a refrigerator, so as to prevent the attachment of a bacterial pollutant and to facilitate removal of the attached bacterial pollutant.

A quaternary ammonium group of the first structural unit may carry out its antimicrobial functionality on contact with bacteria. As the quaternary ammonium group has a structure bonded to the copolymer, it is not consumed and may impart antimicrobial functionality for repeated uses, so that it may improve durability.

The second structural unit may be a repeating unit that forms poly(meth)acrylate segments or polystyrene segments, or modified polystyrene segments, and the like. The second structural unit may act to facilitate mixing the copolymer with the several polymer resins. It is to be understood, however, that the copolymer can have any type of structure, for example, an alternating A-B structure or a block AA-BB type structure.

Generally, the polyoxazoline antifouling functionality is hydrophilic, and there may be associated mixing challenges in preparing a water repellent polymer resin from these compounds. In an exemplary embodiment, oxazoline-based derivatives such as a polyoxazoline, an oxazoline oligomer, or an oxazoline copolymer to provide an antifouling functionality may include coating a composition including an oxazoline-based derivative on the surface of an article. Articles requiring antimicrobial and antifouling properties are produced by extrusion or an injection process. An additional coating may be used on the surface of an extruded material or an injected material, however, additional coatings increase the cost and may decrease the durability of the coated material.

The copolymer according to one embodiment includes a second structural unit as well as an oxazoline group to provide excellent compatibility with a polymer resin. In addition, the copolymer has a polymer functionality that helps prevent the antimicrobial material or the antifouling material from being leached out, and it may be mixed with a resin matrix and directly employed for an extrusion, a co-extrusion, an injection, or a double injection molding process.

In Chemical Formulae 1 and 2, $R^{12}$ may be, for example, a substituted or unsubstituted C1 to C5 alkyl group, for example, a methyl group, an ethyl group, or a propyl group, but is not limited thereto.

In Chemical Formulae 1 and 2, n refers to an average degree of polymerization of the oxazoline structural unit and has the value of about 1 to about 200, for example, the real number of about 1 to about 150, about 1 to about 100, about 1 to about 50, about 1 to about 30, or about 1 to about 20. When n is within the range, the copolymer including the first structural unit may impart an excellent antifouling functionality.

In Chemical Formulae 1 and 2, $G^1$, $G^2$, $G^3$, $G^5$, and $G^6$ may be, for example, each independently, a substituted or unsubstituted C1 to C20 alkyl group, a substituted or unsubstituted C5 to C10 cycloalkyl group, a substituted or unsubstituted C6 to C10 aryl group, or a substituted or unsubstituted C3 to C10 heterocyclic group.

For example, in Chemical Formula 1, at least one of $G^1$, $G^2$, and $G^3$ or in Chemical Formula 2, at least one of $G^5$ and $G^6$ may be a C6 to C30 alkyl group, that is, an alkyl group having 6 or more carbons. For example, in Chemical Formula 1, at least one of $G^1$, $G^2$, and $G^3$ or in Chemical Formula 2, at least one of $G^5$ and $G^6$ may be a C6 to C25 alkyl group, a C6 to C20 alkyl group, a C6 to C15 alkyl group, a C8 to C30 alkyl group, or a C10 to C30 alkyl group, but is not limited thereto. In this case, in the first structural unit, the quaternary ammonium group may have an excellent contact-killing antimicrobial functionality.

In Chemical Formula 2, $G^4$ and $G^7$ are each independently a substituted or unsubstituted C1 to C10 alkylene group, or C1 to C5 alkylene group, C1 to C3 alkylene group, and connect the A to the quaternary ammonium group.

In Chemical Formulae 1 and 2, $X^-$ is an anion that forms a salt with the quaternary ammonium cation. Non-limiting examples of $X^-$ may be $F^-$, $Cl^-$, $Br^-$, $I^-$, $OH^-$, $BF_4^-$, $NO_3^-$, $H_2PO_4^-$, $CF_3COO^-$, $HSO_4^-$, and the like.

In the copolymer, the first structural unit and the second structural unit may be present in a mole ratio of about 1:99 to about 99:1. In an exemplary embodiment, the first structural unit and the second structural unit may be present in a mole ratio of about 10:90 to about 90:10. For example, the first structural unit and the second structural unit may be present in a mole ratio of about 20:80 to about 80:20, for example about 30:70 to about 70:30, for example about 40:60 to about 60:40.

As the first structural unit and the second structural unit are included in the copolymer within the mole ratio, the copolymer may have compatibility with a polymer resin while having antimicrobial/antifouling functionality. The mole ratio of the first structural unit and the second structural unit may be appropriately selected by a person of an ordinary skill in the art to obtain a desirable antimicrobial/antifouling functionality in the final product in which the copolymer is employed, and considering the applicability to the process of easily producing the product. For example, when the copolymer is mixed with the additional polymer resin and employed for the extrusion molding and/or injection molding or the like, the mole ratio of the first structural unit and the second structural unit in the copolymer may be determined based on the amount of the additional polymer resin, the compatibility with a polymer resin, and the antimicrobial/antifouling functionality of the final product or the like.

The Chemical Formula 3 may be, for example a repeating unit of polyalkyl(meth)acrylate. In this case, Y may be a substituted or unsubstituted C1 to C30 alkyl group, specifically a C1 to C5 alkyl group, a C4 to C30 alkyl group, a C6 to C30 alkyl group, a C10 to C30 alkyl group, or a C10 to C20 alkyl group. When Y is the substituent, the copolymer may mix well with a polymer resin, so it is suitable to be employed for an extruded material, a coextruded material, an injected material, or a double-injected material.

The Chemical Formula 4 may be, for example a repeating unit of polystyrene or modified polystyrene. In Chemical Formula 4, Z may be a hydrogen atom, a halogen atom, or an alkyl group, for example a linear or branched C1 to C25 alkyl group, a linear or branched C1 to C20 alkyl group, a linear or branched C1 to C10 alkyl group, or a linear or branched C1 to C5 alkyl group.

The copolymer according to the embodiment may be easily prepared by various known methods by a person of an ordinary skill in the art. For example, the copolymer may be prepared by copolymerization of a first monomer selected from Chemical Formula 11, Chemical Formula 12, and a combination thereof and a second monomer selected from Chemical Formula 13, Chemical Formula 14, and a combination thereof:

Chemical Formula 11

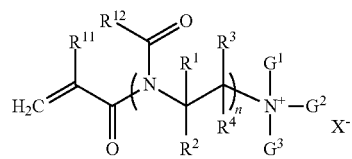

Chemical Formula 12

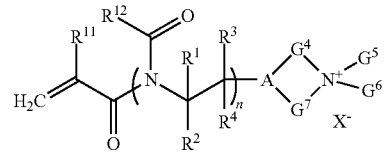

In Chemical Formulae 11 and 12, $R^{11}$ is a hydrogen atom or a methyl group, A is a nitrogen, $R^{12}$ is a substituted or unsubstituted C1 to C10 alkyl group, a substituted or unsubstituted C3 to C20 cycloalkyl group, a substituted or unsubstituted C6 to C20 aryl group, or a substituted or unsubstituted C3 to C20 heterocyclic group, $R^1$ to $R^4$ are the same or different, and are independently hydrogen, a halogen, a hydroxy group, or a substituted or unsubstituted C1 to C5 alkyl group, n is an average value and a real number of 1 to 200, $G^1$, $G^2$, $G^3$, $G^5$, and $G^6$ are the same or different, and are independently a substituted or unsubstituted C1 to C30 alkyl group, a substituted or unsubstituted C3 to C20 cycloalkyl group, a substituted or unsubstituted C6 to C20 aryl group, or a substituted or unsubstituted C3 to C20 heterocyclic group, $G^4$ and $G^7$ are the same or different, and are independently a substituted or unsubstituted C1 to C10 alkylene group, and $X^-$ is a halide ion, a hydroxide ion, a fluorinated boron ion, a nitrate ion, a phosphate salt ion, a trifluoroacetate ion, or a sulfate ion.

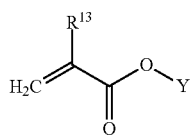

Chemical Formula 13

In Chemical Formula 13, $R^{13}$ is a hydrogen atom or a methyl group and Y is a substituted or unsubstituted C1 to C30 alkyl group, a substituted or unsubstituted C3 to C30 cycloalkyl group, a substituted or unsubstituted C6 to C30 aryl group, or a substituted or unsubstituted C3 to C30 heterocyclic group.

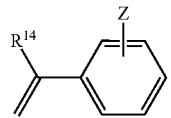

Chemical Formula 14

In Chemical Formula 14, $R^{14}$ is a hydrogen atom or a methyl group and Z is a hydrogen atom, a substituted or unsubstituted linear or branched C1 to C30 alkyl group, or a halogen atom.

The copolymerization may be generally performed by a solution polymerization, a bulk polymerization, but may be performed by the known method in the art selected from an emulsion polymerization, a suspension polymerization, a massive polymerization, or the like. For example, the polymerization may be performed by contacting the first monomer, the second monomer, the catalyst, and a radical initiator in a single solvent such as tetrahydrofuran, ethanol, and the like or a mixed solvent thereof and agitating the same at about 50° C. to about 80° C. for about 3 to 20 hours depending on the monomer according to Chemical Formula 13 or Chemical Formula 14.

The first monomer may be prepared by reacting an initiator represented by Chemical Formula 31, an oxazoline-based monomer represented by Chemical Formula 31, and a terminator represented by Chemical Formula 33 or Chemical Formula 34.

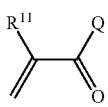

Chemical Formula 31

In Chemical Formula 31, $R^{11}$ is a hydrogen atom or a methyl group and Q is F, Cl, Br, or I.

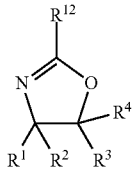

Chemical Formula 32

In Chemical Formula 32, $R^{12}$ is a substituted or unsubstituted C1 to C10 alkyl group, a substituted or unsubstituted C3 to C20 cycloalkyl group, a substituted or unsubstituted C6 to C20 aryl group, or a substituted or unsubstituted C3 to C20 heterocyclic group, and $R^1$ to $R^4$ are the same or different and are independently a hydrogen atom, a halogen atom, a hydroxy group, or a substituted or unsubstituted C1 to C5 alkyl group.

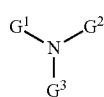

Chemical Formula 33

In Chemical Formula 33, $G^1$ to $G^3$ are the same or different and are independently a substituted or unsubstituted C1 to C30 alkyl group, a substituted or unsubstituted C3 to C20 cycloalkyl group, a substituted or unsubstituted C6 to C20 aryl group, or a substituted or unsubstituted C3 to C20 heterocyclic group.

Chemical Formula 34

In Chemical Formula 34, $G^5$ and $G^6$ are the same or different and are independently a substituted or unsubstituted C1 to C30 alkyl group, a substituted or unsubstituted C3 to C20 cycloalkyl group, a substituted or unsubstituted C6 to C20 aryl group, or a substituted or unsubstituted C3 to C20 heterocyclic group, $G^4$ and $G^7$ are the same or different, and are independently a substituted or unsubstituted C1 to C10 alkylene group.

The first monomer may be produced by mixing the initiator represented by Chemical Formula 31 and the oxazoline-based monomer represented by Chemical Formula 32; polymerizing the same at about 50° C. to about 120° C. for about 1 hour to about 24 hours; subsequently, adding the terminator represented by Chemical Formula 33 or Chemical Formula 34 and reacting the same at about 50° C. to about 120° C. for about 1 hour to about 24 hours; and then by purifying and drying the resultant product.

The initiator represented by Chemical Formula 31 may be, for example, acryloyl halide, or methacryloyl halide, but is not limited thereto. The halide may be fluoride, chloride, bromide, iodide, but is not limited thereto.

The oxazoline-based monomer represented by Chemical Formula 32 may be, for example, 2-methyl-2-oxazoline, 2-ethyl-2-oxazoline, 2-propyl-2-oxazoline, or 2-isopropyl-2-oxazoline, but is not limited thereto.

During the synthesis of the first monomer, the oxazoline-based monomer represented by Chemical Formula 32 may have an average degree of polymerization of about 1 to 200, for example, about 2 to 100, for example, about 2 to 50. In this case, the first monomer may impart the excellent antifouling functionality.

The terminator may be for example, selected from a compound represented by Chemical Formula 33, a compound represented by Chemical Formula Chemical Formula 34, or a combination thereof. When the terminator is the compound of Chemical Formula 33, the monomer of Chemical Formula 11 is prepared, and when the terminator is the compound of Chemical Formula 34, the monomer of Chemical Formula 12 is prepared. For another example, when the compound of Chemical Formula 33 and the compound of Chemical Formula 34 are used as the terminator, a monomer mixture of the monomer of Chemical Formula 11 and the monomer of Chemical Formula 12 may be prepared.

The second monomer may be easily prepared by a known method or is commercially available.

In the second monomer, Y of Chemical Formula 13 or Z of Chemical Formula 14 for example may be a C1 to C5 alkyl group, a C4 to C30 alkyl group, a C10 to C30 alkyl group, or a C20 to C30 alkyl group. In this case, the second monomer may impart compatibility between the copolymer and the resin matrix.

During the copolymerization, the first monomer and the second monomer may be used in a mole ratio of about 1:99 to about 99:1, for example, about 10:90 to about 90:10, for example about 20:80 to about 80:20, for example about 30:70 to about 70:30, or about 40:60 to about 60:40. When the first monomer and the second monomer are copolymerized within that range, it may provide a copolymer having an antimicrobial/antifouling functionality and compatibility with a polymer resin.

In another embodiment, a composition including the copolymer is provided.

As described above, the copolymer according to one embodiment includes a first structural unit to provide an antimicrobial/antifouling functionality; and also it includes a second structural unit to provide compatibility with the additional polymer resin. The copolymer may form a resin composition capable of being employed for an extrusion, co-extrusion, injection, double injection molding, or the like, alone or by mixing with an additional thermoplastic polymer.

When the composition further includes the additional thermoplastic polymer, the copolymer may be used as an additive to provide an antimicrobial/antifouling functionality to the composition. The copolymer has excellent compatibility with the additional thermoplastic polymer and may impart a long-term antimicrobial/antifouling functionality in the composition. Thus, the composition has continuous antimicrobial/antifouling functionality and is durable such that the antimicrobial material or the antifouling material is not leached, so as to be employed for extrusion or injection molding or the like.

The composition is suitable to be employed as an exterior or interior material for a home appliance such as a washing tub of a washing machine, an interior material of a refrigerator, an external or internal material of an air conditioner, and a dust bag of cleaning machine, which requires antimicrobial/antifouling functionality and durability. In addition, the composition may be employed for a medical appliance such as a hospital bed, a catheter, artificial teeth, a splint, and the like, a 3D printing product such as a 3D-printable antimicrobial synthetic resin, a mobile product such as a mobile phone, a structure, a fiber, a membrane, or other various daily supplies.

The composition according to one embodiment may be a composite including the copolymer and the additional thermoplastic polymer. The copolymer may be dispersed in the additional thermoplastic polymer, and in this case, the copolymer may be a kind of additive and the additional thermoplastic polymer may be a kind of matrix resin.

The additional thermoplastic polymer is not particularly limited and may be at least one thermoplastic polymer selected from polyolefin, polyalkyl(meth)acrylate, polyacrylonitrile, polystyrene, polyvinyl chloride, polyvinylidene chloride, silicone resin, polysulfone, polycarbonate, a rubber modified vinyl-based copolymer, polyamide, polyester, thermoplastic polyurethane, and a copolymer thereof. The copolymer is compatible with such a thermoplastic polymer resin.

The thermoplastic polymer may be used in an amount of about 1 wt % to about 99.9 wt %, for example, about 10 wt % to about 99.9 wt %, for example about 20 wt % to about 99.9 wt %, for example about 30 wt % to about 99.9 wt %, for example about 40 wt % to about 99.9 wt %, or about 50 wt % to about 99 wt % based on the total weight of the composition, but is not limited thereto.

When the composition includes the additional thermoplastic polymer within the above-described range, it may continuously impart the excellent antimicrobial/antifouling functionality and may be molded by extrusion, co-extrusion, injection, or double injection, and the like.

In the composition, the first structural unit of the copolymer is a moiety capable of performing the antimicrobial/antifouling functionality, and it may be included in about 0.1 wt % to about 50 wt % based on the total weight of the composition. For example, the first structural unit may be used in an amount of about 0.2 wt % to about 30 wt %, for example about 0.3 wt % to about 25 wt %, for example about 0.4 wt % to about 20 wt %, for example about 0.5 wt % to about 15 wt %, for example about 0.5 wt % to about 10 wt %, for example about 0.5 wt % to about 9 wt %, for example about 0.5 wt % to about 8 wt %, for example about 0.5 wt % to about 7 wt %, for example about 0.5 wt % to about 6 wt %, or about 0.5 wt % to about 5 wt % based on the total weight of the composition.

As understood from the Examples described below, when the first structural unit is present only in an amount of about 2.5% in the final product, bacteria such as *Escherichia Coli* (*E. coli*) is removed at greater than or equal to about 99.9%. In other words, when the copolymer including the first structure unit is included in the final composition within the described range, the composition may have both the excellent antimicrobial/antifouling functionality and the excellent miscibility with an additional polymer resin or the like.

As the composition includes a copolymer in which a first structural unit showing the antimicrobial/antifouling functionality and a second structural unit showing the compatibility with a resin are copolymerized, the moiety having the antimicrobial/antifouling functionality is not leached or consumed, so the long-term antimicrobial/antifouling functionality may be maintained. Thereby, the product is more durable.

Another embodiment provides an article having an antimicrobial/antifouling functionality and that is manufactured from the composition.

Unlike an antimicrobial/antifouling product applied by a coating method, a resin itself forming the article has the antimicrobial/antifouling functionality, so the article is not harmful to the human body because there is no leaching during use, i.e., the article is durable and the antimicrobial/antifouling properties are not consumed. In addition, because these properties are not leached or consumed, it may stably provide a product imparting the antimicrobial/antifouling functionality over time.

The article is also manufactured by a simple method.

The copolymer or a composition including the copolymer and the additional polymer may be formed by extrusion or co-extrusion; or the composition is formed to a pallet by extrusion molding or the like, then it is injected or double-injected into a desirable shape according to injection molding method or the like. For example, when the composition includes an additional polymer, the copolymer and the additional polymer are input into one extruder and extruded together, so that it may be easily processed into an article having the antimicrobial/antifouling functionality. The method is clear and easily known by a person having ordinary skill in the art, so it may easily product the molded article having the antimicrobial/antifouling functionality according to the embodiment using the method.

The article may have excellent antimicrobial functionality. For example, the article may have a greater than or equal to about 85% antimicrobial rate for *Escherichia coli*, for example, greater than or equal to about 88%, for example, greater than or equal to about 90%, for example, greater than or equal to about 95%, or greater than or equal to about 99%, wherein the antimicrobial rate for *Escherichia coli* is calculated by the antimicrobial test according to ISO 22196.

Also, the article may have antifouling functionality. For example, the pollution level of the article may be decreased in greater than or equal to about 20%, for example, greater than or equal to about 21%, for example, greater than or equal to about 22%, for example, greater than or equal to about 23%, for example, less than or equal to about 99%, for example, less than or equal to about 90%, or less than or equal to about 80%, compared to the pollution level of an article treated with no antifouling treatment.

The article treated with no antifouling treatment refers to the article obtained from a thermoplastic resin used as a comparative reference without the copolymer. Examples of the thermoplastic resin may include a polyolefin or the like. When the article according to one embodiment is obtained from the composition including the copolymer and the additional thermoplastic polymer, the additional thermoplastic polymer may be the same thermoplastic resin that is used as a comparative reference.

According to an exemplary embodiment, the pollution test of the article may be performed, for example, as follows: by immersing the article in a contaminated water standard in which 0.9 wt % of a detergent, 0.8 wt % of second-cut cotton linters and 0.04 wt % of dust are mixed in distilled water for 2 minutes and dried for 15 minutes, each of which steps are repeated 3 times. The article is then weighted to calculate the amount of attached pollutant, and a ratio of the weight of the attached amount of pollutant to the weight of the article before immersion in the contaminated water standard is evaluated to determine the amount of pollution.

EXAMPLES

The following Examples and Comparative Examples are provided in order to highlight characteristics of one or more exemplary embodiments, and are for illustrative purposes. The Examples and Comparative Examples are not intended to limit the scope of the embodiments, nor are the Comparative Examples to be construed as being outside the scope of the exemplary embodiments. Further, it will be understood that the exemplary embodiments are not limited to the particular details described in the Examples and Comparative Examples.

Synthesis Example 1: Synthesis of First Monomer

An initiator of 1 equivalent of acryloyl chloride, 1 equivalent of potassium iodide, and an oxazoline-based monomer of 15 equivalents of methyl oxazoline were contacted in acetonitrile, and the oxazoline-based monomer was polymerized at a temperature of 80° C. under atmospheric pressure for 20 hours. As a terminator, dimethyldodecylamine (DDA: N,N-dimethyldodecylamine) in chloroform is added thereto and reacted at 80° C. for 20 hours. The synthesized product, the compound represented by Chemical Formula 41 is precipitated using diethylether, and then filtered and dried. The product having an average degree of polymerization of 15 (in Chemical Formula 41, n is 15) is obtained in a yield of 90 mass %.

Chemical Formula 41

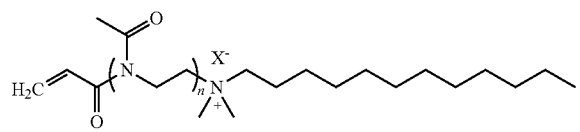

Synthesis Example 2: Synthesis of First Monomer

A first monomer is synthesized, and the compound represented by Chemical Formula 41 having an average degree of polymerization of 5 (in Chemical Formula 41, n is 5) is obtained in a yield of 95 mass % in accordance with the same procedure as in Synthesis Example 1, except that 5 equivalent of methyl oxazoline is used as an oxazoline-based monomer.

Synthesis Example 3: Synthesis of First Monomer

A first monomer is synthesized, and the compound represented by Chemical Formula 42 having an average degree of polymerization of 15 (in Chemical Formula 42, n is 15) is obtained in a yield of 95 mass % in accordance with the same procedure as in Synthesis Example 1, except that 1 equivalent of methacryloyl chloride is used as an initiator.

Chemical Formula 42

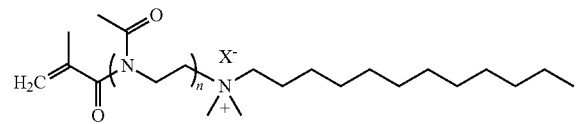

Example 1: Synthesis of Copolymer

The compound represented by Chemical Formula 41 having an average degree of polymerization of 5 obtained from Synthesis Example 2 and octadecyl acrylate (ODA) are contacted in a mixed solvent of tetrahydrofuran and ethanol in a mass ratio of 1:1 and then mixed with 0.5 mass % of azobisisobutyronitrile (AIBN) initiator. The mixture was held at 70° C. for 15 hours, and the product was then precipitated and dried to provide a copolymer represented by Chemical Formula 43 (n is 5) in a yield of 85%.

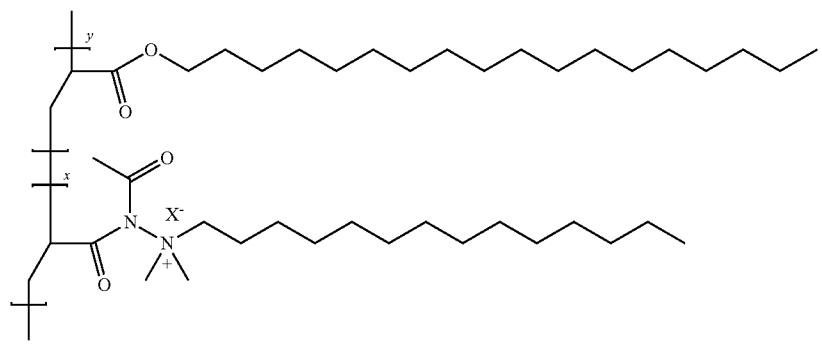

Chemical Formula 43

Example 2: Synthesis of Copolymer

A copolymer is prepared in accordance with the same procedure as in Example 1, except that the compound represented by Chemical Formula 42 (n is 15) obtained from Synthesis Example 3 is used instead of is the compound represented by Chemical Formula 41.

Example 3: Synthesis of Copolymer

A copolymer is prepared in accordance with the same procedure as in Example 1, except that the compound represented by Chemical Formula 41 (n is 15) having an average polymerization degree of 15 obtained from Synthesis Example 1 and octadecyl acrylate (ODA) initiator are mixed in a mass ratio of 3:1 and copolymerized.

Example 4: Synthesis of Copolymer

A copolymer is prepared in accordance with the same procedure as in Example 1, except that methylmethacrylate (MMA) is used instead of octadecyl acrylate (ODA) as an initiator.

Example 5: Synthesis of Copolymer

A copolymer is prepared in accordance with the same procedure as in Example 2, except that methylmethacrylate (MMA) is used instead of octadecyl acrylate (ODA) as an initiator.

Preparation Examples 1 to 5: Manufacture of Article

Each of the copolymers obtained from the Examples 1 to 5 and a polypropylene resin are mixed in a weight ratio shown in Table 1, respectively, and placed in a twin-screw extruder and melt blended to provide a mixed composition injection molded specimen of each copolymer. The mixed composition injection specimen each had the dimensions 63 mm×13 mm×2.2 mm (width×length×thickness).

Evaluation Example 1: Antimicrobial Evaluation

The antimicrobial activity of each injection molded specimen obtained from Preparation Examples 1 to 5 are measured for antimicrobial activity against *Escherichia coli* (*E. coli*) using the antimicrobial test according to ISO 22196, and the results are shown in Table 1.

TABLE 1

|  | Composition | Amount of first structural unit | Antimicrobial Rate (*E. coli*) |
| --- | --- | --- | --- |
| Control | PP (polypropylene) (100 wt %) | 0% | 0% |
| Preparation Example 1 | PP (95 wt %) + Example 1 (5 wt %) | 2.5% | 99.9% |
| Preparation Example 2 | PP (95 wt %) + Example 2 (5 wt %) | 2.5% | 95% |
| Preparation Example 3 | PP (95 wt %) + Example 3 (5 wt %) | 3.75% | 88% |
| Preparation Example 4 | PP (95 wt %) + Example 4 (5 wt %) | 2.5% | 99% |
| Preparation Example 5 | PP (95 wt %) + Example 5 (5 wt %) | 2.5% | 90% |

Table 1 illustrates the antimicrobial activity for each of the injection molded specimens, as determined by the antimicrobial rate of each specimen. A polypropylene injection molded specimen is used as a control group and has an antimicrobial activity of 0%. The injection molded specimens according to Preparation Examples 1 to 5, each including the respective copolymers according to Examples 1 to 5, have an antimicrobial activity of greater than or equal to about 88%.

Evaluation Example 2: Antifouling Evaluation 0.9 wt % of a detergent (Tide, Procter & Gamble), 0.8 wt % of second-cut cotton linters (Powder Technologies Inc.), and 0.04 wt % of a dust (JIS Test Powders1-class8, APPIE) are added into 1 liter (L) of distilled water and then stirred at 300 rpm to provide a contaminated water standard.

The copolymer obtained from Preparation Example 1 and a polypropylene specimen are each dipped in the contaminated water standard for 2 minutes and then dried for 15 minutes, and this procedure is repeated 3 times. Each sample was then weighed to calculate the attached amount of pollutes. The weight of pollutes attached to the specimen obtained from Preparation Example 1 is 23% less than the weight of pollutes attached to the polypropylene specimen. Thereby, it is confirmed that the pollution level of a specimen according to Preparation Example 1 is decreased in greater than or equal to about 20% as compared to the pollution level of the reference polymer resin such as polypropylene.

Evaluation Example 3: Compatibility Evaluation

Figure 2:
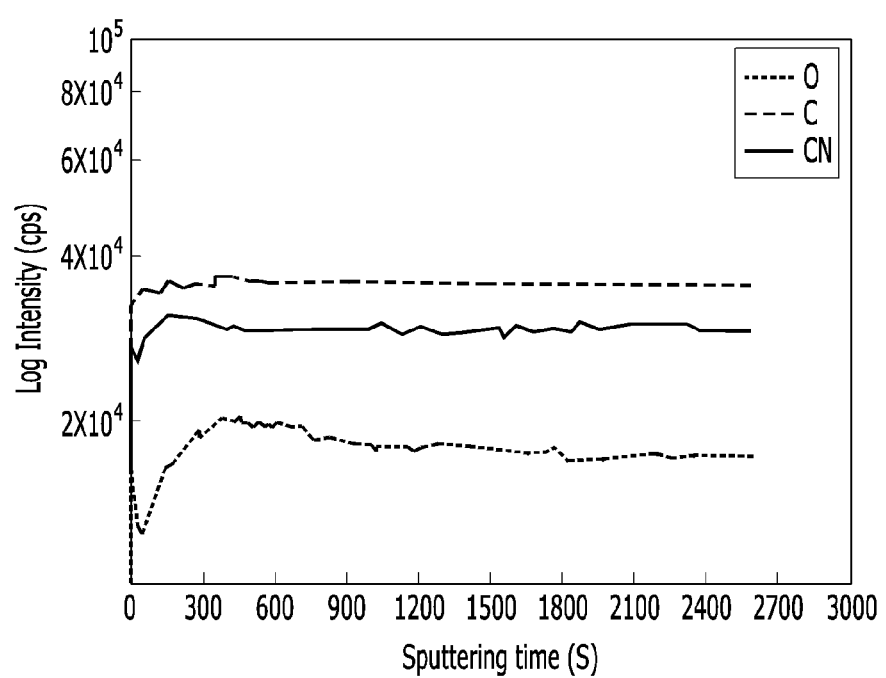
FIG. 2 is a graph of log intensity (counts per second, cps) versus sputtering time (seconds, s) and is a Time-of-Flight secondary ion mass spectrometry graph for an injection molded specimen obtained from Preparation Example 1.

The polypropylene injection specimen fabricated for the control test and the injection specimen obtained from Preparation Example 1 are measured for concentrations of carbon, oxygen, and nitrogen using a Time-of-Flight secondary ion mass spectrometer (TOF-SIMS) method, and the results are shown in FIG. 1 and FIG. 2, respectively.

Referring to FIG. 1 and FIG. 2, it is confirmed that the polymer including oxazoline is not present in a thickness direction (sputtering time) in the PP injection specimen used as a control group, so nitrogen and oxygen are not present in FIG. 1. However, nitrogen and oxygen are found in a constant concentration (intensity) in a thickness direction in FIG. 2. In other words, it is confirmed that nitrogen and oxygen, which are atoms of oxazoline, are uniformly dispersed in the specimen. In other words, it is understood that the copolymers according to Example 1 and the like are compatible with the matrix resin.

While this disclosure has been described in connection with what is presently considered to be practical exemplary embodiments, it is to be understood that the scope of the disclosure is not limited to the disclosed embodiments, but, on the contrary, is intended to cover various modifications and equivalent arrangements included within the spirit and scope of the appended claims.

What is claimed is:

1. A copolymer comprising:
a first structural unit selected from Chemical Formula 1, Chemical Formula 2, and a combination thereof and
a second structural unit selected from Chemical Formula 3, Chemical Formula 4, and a combination thereof:

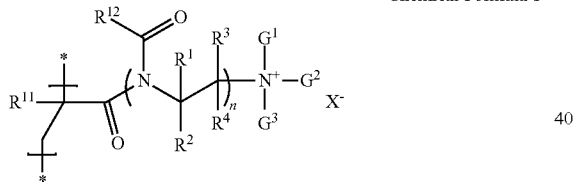

Chemical Formula 1

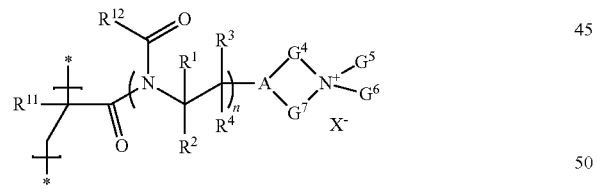

Chemical Formula 2 wherein, in Chemical Formulae 1 and 2,
$R^{11}$ is a hydrogen atom or a methyl group,
A is nitrogen,
$R^{12}$ is a substituted or unsubstituted C1 to C10 alkyl group, a substituted or unsubstituted C3 to C20 cycloalkyl group, a substituted or unsubstituted C6 to C20 aryl group, or a substituted or unsubstituted C3 to C20 heterocyclic group,
$R^1$ to $R^4$ are the same or different, and are independently a hydrogen atom, a halogen atom, a hydroxy group, or a substituted or unsubstituted C1 to C5 alkyl group,
n is an average value and a real number of 1 to 200,
$G^1$, $G^2$, $G^3$, $G^5$, and $G^6$ are the same or different, and are independently a substituted or unsubstituted C1 to C30 alkyl group, a substituted or unsubstituted C3 to C20 cycloalkyl group, a substituted or unsubstituted C6 to C20 aryl group, or a substituted or unsubstituted C3 to C20 heterocyclic group,
$G^4$ and $G^7$ are the same or different, and are independently a substituted or unsubstituted C1 to C10 alkylene group, and
$X^-$ is a halide ion, a hydroxide ion, a fluorinated boron ion, a nitrate ion, a phosphate salt ion, a trifluoroacetate ion, or a sulfate ion,

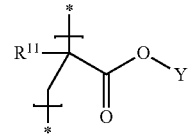

Chemical Formula 3 wherein, in Chemical Formula 3,
$R^{13}$ is a hydrogen atom or a methyl group, and
Y is a substituted or unsubstituted C1 to C30 alkyl group, a substituted or unsubstituted C3 to C30 cycloalkyl group, a substituted or unsubstituted C6 to C30 aryl group, or a substituted or unsubstituted C3 to C30 heterocyclic group,

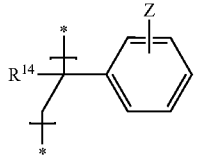

Chemical Formula 4 wherein, in Chemical Formula 4,
$R^{14}$ is a hydrogen atom or a methyl group, and
Z is a hydrogen atom, a substituted or unsubstituted C1 to C30 alkyl group, or a halogen atom.

2. The copolymer of claim 1 wherein, in Chemical Formula 1 or in Chemical Formula 2, $R^{12}$ is a C1 to C5 alkyl group.

3. The copolymer of claim 1, wherein at least one of $G^1$ to $G^3$ in Chemical Formula 1 or at least one of $G^5$ and $G^6$ in Chemical Formula 2 is a C6 to C30 alkyl group.

4. The copolymer of claim 1, wherein in Chemical Formula 1, one of $G^1$ to $G^3$ is a C6 to C30 alkyl group and the other two of $G^1$ to $G^3$ are each independently a C1 to C3 alkyl group, or, in Chemical Formula 2, one of $G^5$ and $G^6$ is a C6 to C30 alkyl group and the other of $G^5$ and $G^6$ is a C1 to C3 alkyl group.

5. The copolymer of claim 1, wherein the first structural unit and the second structural unit are present in a mole ratio of about 1:99 to about 99:1.

6. The copolymer of claim 1, wherein Y of Chemical Formula 3 or Z of Chemical Formula 4 is a substituted or unsubstituted C1 to C30 alkyl group.

7. The copolymer of claim 1, wherein a mass average molecular weight of the copolymer is about 1,000 grams per mole to about 1,000,000 grams per mole.

8. A composition comprising the copolymer of claim 1.

9. The composition of claim 8, wherein the composition further comprises at least one thermoplastic polymer selected from a polyolefin, a polyalkyl(meth)acrylate, a polyacrylonitrile, a polystyrene, a polyvinyl chloride, a polyvinylidene chloride, a silicone resin, a polysulfone, a polycarbonate, a rubber modified vinyl-based copolymer, a polyamide, a polyester, a polyurethane, and a copolymer thereof.

10. The composition of claim 9, wherein the thermoplastic polymer is present in an amount of about 1 weight percent to about 99.9 weight percent based on a total weight of the composition.

11. The composition of claim 9, wherein the first structural unit of the copolymer is present in an amount of about 0.1 wt % to about 50 wt % based on a total weight of the composition.

12. The composition of claim 9, wherein the first structural unit of the copolymer is present in an amount of about 0.5 weight percent to about 10 weight percent based on a total weight of the composition.

13. An article comprising the composition of claim 8.

14. The article of claim 13, wherein the article is manufactured by extrusion, co-extrusion, injection molding, or double injection molding processes.

15. The article of claim 13, wherein the article has a greater than or equal to about 85% antimicrobial rate for *Escherichia coli*, as measured by the antimicrobial test according to ISO 22196.

16. The article of claim 13, wherein a pollution level of the article is reduced by greater than or equal to about 20% compared to a pollution level of an article without the composition of claim 8.

17. A method of preparing a copolymer comprising:
copolymerizing
a first monomer selected from Chemical Formula 11, Chemical Formula 12, and a combination thereof and
a second monomer selected from Chemical Formula 13, Chemical Formula 14, and a combination thereof:

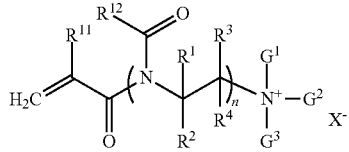

Chemical Formula 11

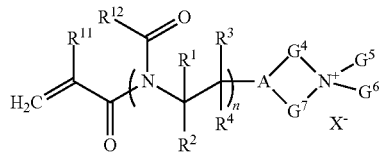

Chemical Formula 12 wherein, in Chemical Formulae 11 and 12,
$R^{11}$ is a hydrogen atom or a methyl group,
A is a nitrogen,
$R^{12}$ is a substituted or unsubstituted C1 to C10 alkyl group, a substituted or unsubstituted C3 to C20 cycloalkyl group, a substituted or unsubstituted C6 to C20 aryl group, or a substituted or unsubstituted C3 to C20 heterocyclic group, $R^1$ to $R^4$ are the same or different, and are independently a hydrogen atom, a halogen atom, a hydroxy group, or a substituted or unsubstituted C1 to C5 alkyl group,
n is an average value and a real number of 1 to 200,
$G^1$, $G^2$, $G^3$, $G^5$, and $G^6$ are the same or different, and are independently a substituted or unsubstituted C1 to C30 alkyl group, a substituted or unsubstituted C3 to C20 cycloalkyl group, a substituted or unsubstituted C6 to C20 aryl group, or a substituted or unsubstituted C3 to C20 heterocyclic group,
$G^4$ and $G^7$ are the same or different, and are independently a substituted or unsubstituted C1 to C10 alkylene group, and
$X^-$ is a halide ion, a hydroxide ion, a fluorinated boron ion, a nitrate ion, a phosphate salt ion, a trifluoroacetate ion, or a sulfate ion,

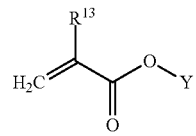

Chemical Formula 13 wherein in Chemical Formula 13,
$R^{13}$ is a hydrogen atom or a methyl group, and
Y is a substituted or unsubstituted C1 to C30 alkyl group, a substituted or unsubstituted C3 to C30 cycloalkyl group, a substituted or unsubstituted C6 to C30 aryl group, or a substituted or unsubstituted C3 to C30 heterocyclic group,

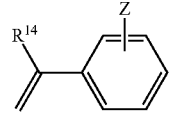

Chemical Formula 14 wherein in Chemical Formula 14,
$R^{14}$ is a hydrogen atom or a methyl group and
Z is a hydrogen atom, a substituted or unsubstituted linear or branched C1 to C30 alkyl group, or a halogen atom.

18. The method of claim 17, wherein, in Chemical Formula 11, one of $G^1$ to $G^3$ is a C6 to C30 alkyl group and the other two of $G^1$ to $G^3$ are each independently a C1 to C3 alkyl group, or, in Chemical Formula 2, one of $G^5$ and $G^6$ is a C6 to C30 alkyl group and the other of $G^5$ and $G^6$ is a C1 to C3 alkyl group.

19. The method of claim 17, wherein the first monomer and the second monomer are present in a mole ratio of about 1:99 to about 99:1.

20. The method of claim 17, wherein a mass average molecular weight of the copolymer is about 1,000 grams per mole to about 1,000,000 grams per mole.

* * * * *